United States Patent [19]

Zigelbaum

[11] Patent Number: 5,690,486
[45] Date of Patent: Nov. 25, 1997

[54] DENTAL TOOTH COLOR DETECTOR APPARATUS AND METHOD

[75] Inventor: Sheldon D. Zigelbaum, Boston, Mass.

[73] Assignee: Dentalase Corporation, Newton, Mass.

[21] Appl. No.: 508,868

[22] Filed: Jul. 28, 1995

[51] Int. Cl.$^6$ ............................................. A61C 1/00
[52] U.S. Cl. ................................................ 433/29; 356/405
[58] Field of Search ........................ 433/26, 29, 203.1,
433/215; 364/413.28; 356/402, 405, 406, 408

[56] References Cited

U.S. PATENT DOCUMENTS

| | | | |
|---|---|---|---|
| 4,096,217 | 6/1978 | Roll | 356/405 |
| 4,654,974 | 4/1987 | O'Brien | 433/26 |
| 4,836,674 | 6/1989 | Lequime et al. | 433/26 |
| 5,383,020 | 1/1995 | Vieillefosse | 356/326 |

FOREIGN PATENT DOCUMENTS

| | | | |
|---|---|---|---|
| 9002929 | 3/1990 | WIPO | 433/203.1 |
| 9102955 | 3/1991 | WIPO | 433/29 |

*Primary Examiner*—Cary E. O'Connor
*Attorney, Agent, or Firm*—Cesari and McKenna, LLP

[57] ABSTRACT

The present invention relates to a dental device which detects the color of a damaged tooth and automatically determines the proper restorative dental material to be used to repair the damaged tooth. The device illuminates the tooth with light and detects the various color components of light reflected off the tooth. Signals indicative of the various color components are then processed and compared against known reference signal values indicative of the color of various restorative materials in order to determine which of the plurality of restorative dental materials best matches the color of the tooth. The device then displays a message indicative of the chosen material. The detector is preferably a lightweight, hand-held, battery powered device, which includes a wand assembly which is placed against the tooth. A disposable, replaceable, protective sheath is placed over the wand to ensure the health and safety of the patient. The sheath includes a light absorbing dark material which reduces, and preferably eliminates, the amount of ambient light which is reflected off the tooth and detected by the device when the wand is being used.

14 Claims, 5 Drawing Sheets

DENTAL TOOTH COLOR DETECTOR APPARATUS AND METHOD

TECHNICAL FIELD

The present invention relates to color detection, and in particular to a device for detecting the color of a dental patient's damaged tooth in order to determine the color of the restorative material to be used in a cosmetic dental procedure to repair the damaged tooth.

BACKGROUND ART

In the field of cosmetic dentistry, a damaged tooth is repaired (e.g., replaced or capped) with a composite/porcelain material which the dentist shapes. Since the color of teeth varies, the composite/porcelain material must be available in a number of different colors so the repaired tooth looks natural.

In order to select the proper color, the dentist manually compares a template illustrating the various colors of the available restorative material against the tooth to be repaired. Such a manual procedure is clearly suspect since the important color matching decision is left to the subjective determination of the dentist. Along with the subjectiveness of the dentist, lighting conditions and other factors can often lead to the selection of a less than optimum color.

To assist the dentist in determining the proper tooth color, U.S. Pat. No. 3,986,777 to Kenneth A. Roll discloses a tristimules colorimeter which is placed against the damaged tooth. The colorimeter includes a light source (i.e., tungsten halogen lamp) which generates light that is filtered to provide a light beam having a relatively uniform distribution which is then input to a light pipe, such as a bifurcated fiber optic bundle. The uniform beam of light propagates along the bundle and exits a glass rod which diffuses the light and provides a light beam that strikes the tooth. The diffuse beam of light is reflected off the tooth back to a detector where the red, green and blue components of the reflected light are measured. The device then displays three signal values (i.e., voltage values) indicative of the red, green and blue color components which the user uses to determine the color of the moth, and hence the appropriate restorative dental material.

Several problems have prevented colorimeters such as the one disclosed in the '777 patent from gaining acceptance in the dental community. First, a user of the colorimeter disclosed in the '777 patent has to take the three signal values indicative of the red, green, and blue color components and manually correlate the data with color information indicative of the colors of available restorative material. Therefore, even though the dentist has the benefit of measured color information, the information still has to be manually processed by the dentist or dental assistant to determine the proper restorative material. A further problem with the manual processing is that it presents an opportunity for someone to incorrectly match the data from the colorimeter to the information about the restorative material, and therefore lead to the selection of the wrong material. Such an error can be further compounded if the dentist starts the restorative procedure before realizing that the color match is incorrect, thus wasting his precious time, and loosing the confidence of the patient.

A second problem with the colorimeter disclosed in the '777 patent is that the probe is not suitable for use under current health and safety standards. That is, any component which comes in contact with the patient should be sterile and replaced after each patient.

Therefore, there exists a need a for a device which a dentist or dental assistant can use to accurately and automatically determine the proper restorative material to be used to repair a damaged tooth.

DISCLOSURE OF THE INVENTION

An object of the present invention is to provide a device which detects the color of a damaged tooth and automatically determines the proper restorative dental material to be used to repair the damaged tooth.

Another object of the present invention is to provide a device which is easy to use and safe.

According to the present invention, a dental tooth color detector measures the color of a tooth or a region of a tooth by receiving a plurality of light components reflected off the tooth in response to a controlled illumination, the detector processes signals indicative of the plurality of reflected light components to automatically determine which of a plurality of restorative dental materials best matches the color of the tooth, and then displays information indicative of the selected material.

The detector is preferably a lightweight, hand-held, battery powered device comprising a main body which includes device electronics, and a wand which is connected to the main body via a fiber optic bundle.

According to another aspect of the present invention, a disposable, replaceable protective sheath is placed over the wand to ensure the health and safety of the patient. The sheath includes a light absorbing dark material to reduce, and preferably eliminate, the amount of ambient light which is reflected off the tooth and sensed by the detector.

An advantage of the present invention is that it determines the specific restorative material to be used to repair a damaged tooth.

Another advantage is that the present invention can be used by a dental assistant without the assistance of the dentist. This allows the dentist to save his most precious resource, time, while increasing the quality of the color match.

These and other objects, features and advantages of the present invention will become more apparent in light of the following detailed description of a preferred embodiment thereof, as illustrated in the accompanying drawings.

PREFERRED EMBODIMENT FOR CARRYING OUT THE PRESENT INVENTION

Figure 1:
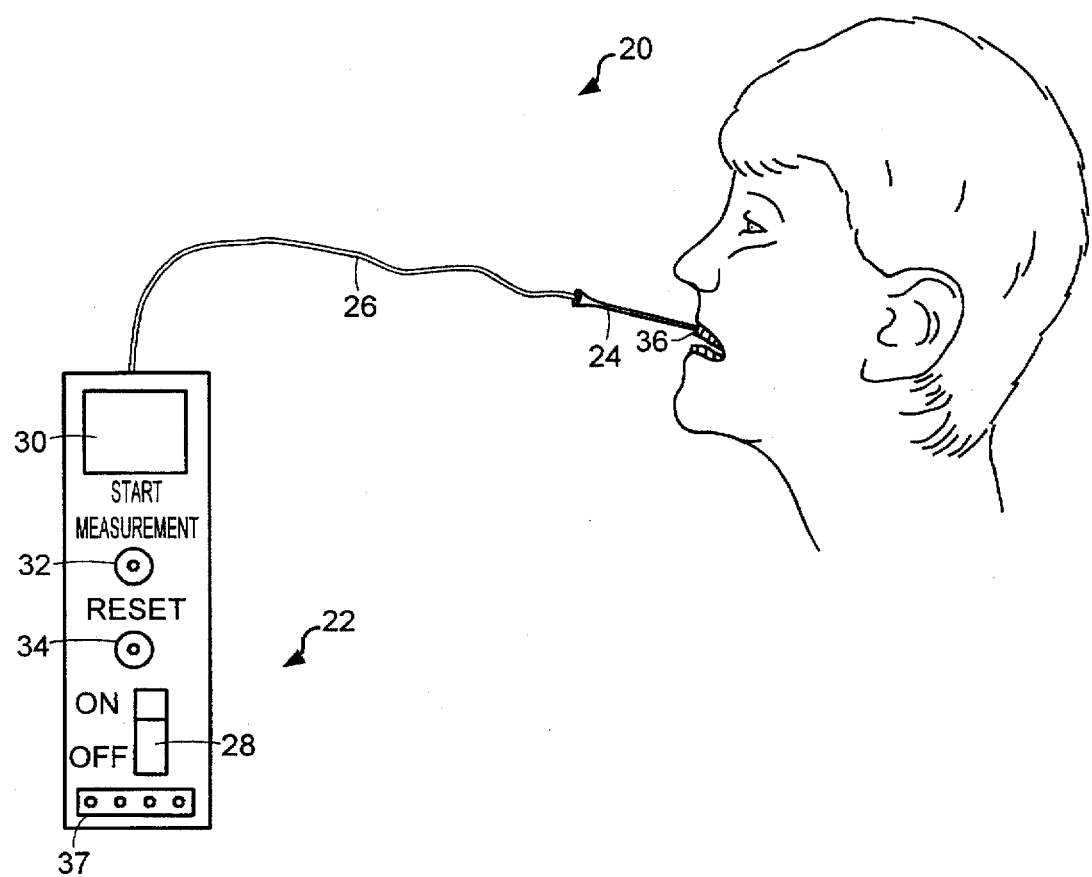
FIG. 1 is a pictorial illustration of a dental tooth color detector.

FIG. 1 is a pictorial illustration of a dental tooth color detector 20. The detector 20 includes a hand-held, battery powered main body assembly 22 which is connected to a hand-held wand 24 through a bifurcated fiber-optic bundle 26. The main body assembly 22 includes system electronics (not shown) and performs the signal processing associated with the present invention. The main body includes an on/off switch 28 and a display 30 (e.g., either an LCD, a TFEL display, etc.) which displays system messages to a user. The main body 22 may also include a reset button 32 and a start measurement button 34.

The main body 22 provides light which propagates within an output path of the bifurcated fiber-optic bundle 26 to the wand 24, where the diffuse light exits and strikes a damaged tooth 36 of a dental patient. Light indicative of the tooth color is reflected back into the wand 24 and routed to the main body 22 via an input path of the fiber optic bundle 26. Glycerin or a like material may be applied to the tooth 36 prior to taking a measurement to break up any specular light. The light is then processed to determine which of a plurality of restorative dental materials is the best color match to the damaged tooth 36. A message indicative of the selected restorative material is then presented on the display 30.

The detector also includes a dual inline package (DIP) switch block 37 containing a plurality of DIP switches (e.g., four). Since there are a number of different manufacturers of restorative material and each manufacturer's product is slightly different, the user sets the DIP switches to the code associated with the manufacturer whose restorative material he will be using. For example, if the dentist is using restorative material from Company X he would input 0000 binary, and for Company Y he would input 0001 binary, etc. How the information from the DIP switches is used shall be discussed herein in further detail.

Figure 2:
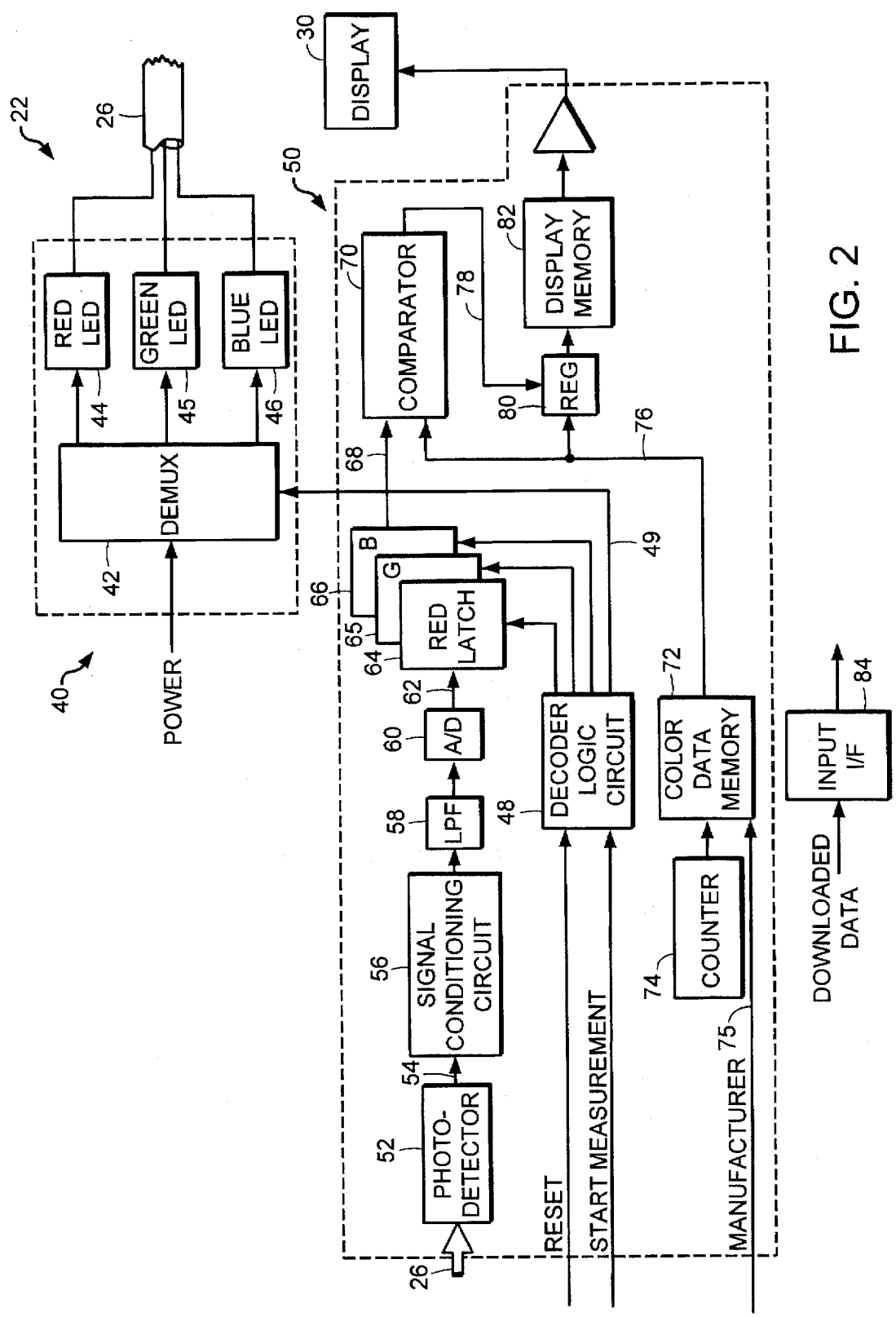
FIG. 2 is a functional block diagram of an embodiment of the dental tooth color detector.

FIG. 2 illustrates a functional block diagram of an embodiment of the main body assembly 22. A light output section 40 includes a demultiplexor 42 which switches a power signal to red, green and blue light emitting diodes, 44–46 respectively, which generate light that is coupled into the output path of the fiber-optic bundle 26. The demultiplexer 42 receives a control signal on a line 49 from a decoder logic circuit 48.

The decoder logic circuit 48 controls the operation and synchronization of the light output section 40 with a light detection and processing section 50. The circuit 48 may include a programmable logic array (PLA) or any other combination of electronic devices (e.g., counters, registers and combinational logic elements) which generate the necessary control signals. The circuit may also be a memory device (e.g., a PROM) along with the necessary combinational and sequential logic devices to create a state machine.

The light detection and processing section 50 includes a photodetector 52 (e.g., a photodiode) which receives the reflected light and provides an electrical signal value on a line 54 indicative of the reflected light. A signal conditioning circuit 56 (e.g., temperature compensation, gain and drift compensation, etc.) then processes the electrical signal value and provides a signal to a low pass filter 58. The filter 58 prevents aliasing and attenuates any high frequency noise. An analog-to-digital converter 60 then samples the signal and provides a digitized signal on a line 62 which is latched into one of a plurality of registers 64–66 dependent upon which LED 44–46 is currently illuminated. That is, when the red LED 44 is illuminated the signal on the line 62 is latched into the red register 64. Similarly, when the green LED is illuminated the signal on the line 62 is latched into the green register 65. Once the red, green and blue signal values have been latched into registers 64–66, the signals indicative of the three components are output in parallel on a line 68 to form a detected color signal value which is input to a comparator 70.

The comparator 70 compares the detected color signal value on the line 68 against a plurality of reference color signal values stored in a non-volatile memory device 72 (e.g., EEPROM). A counter 74 scans through the color data memory 72 to provide the reference color signal values on a line 76. As the counter scans through the memory 72, the comparator continuously compares the signal on the line 68 against the signal on the line 76. Once the comparator 70 detects a match, it provides a signal on a line 78 which latches the reference color signal value on the line 76 into a register 80. The register then provides the address signals to a display memory device 82 which generates a message indicative of the selected restorative material.

In one embodiment (not shown) the comparator 70 may be a set of parallel XOR gates whose outputs feed into an NAND gate whose output is active high (e.g., 5 vdc) when a match has been detected.

The plurality of reference color signal values stored in the color data memory 72 are indicative of the color of available restorative dental materials from a variety of manufactures. For example, Company X may provide restorative material in twenty different colors while Company Y only provides sixteen different colors. To select the manufacturer whose restorative material he will use, the user sets the switches in the DIP switch block 37 (FIG. 1) which provides a signal on a line 75. This signal can be used to define the most significant bits (MSB) for the address to the color data memory 72.

Since the color shades from the manufacturers change occasionally and new products lines are added, the tooth color detector 20 may also include a data input interface 84 (e.g., a serial or parallel port) which allows the color information indicative of the new products to be downloaded into the device 20. For example, the detector 20 can be connected to a standard personal computer (not shown) and the new data can be downloaded from the PC and stored in the color data memory 72. The display memory will also have to be updated during the downloading to contain the appropriate alphanumeric message indicative of the new materials.

Figure 3:
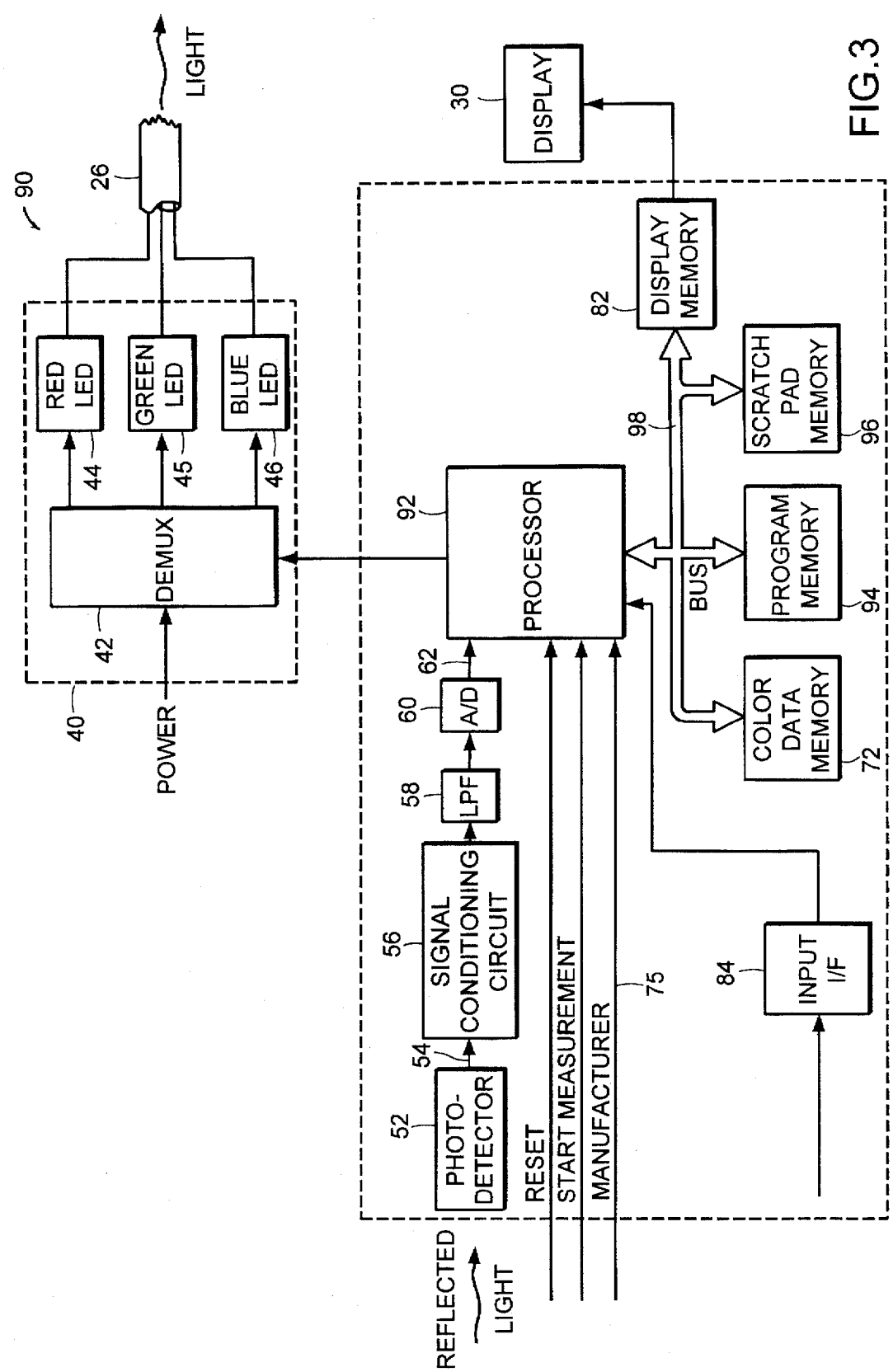
FIG. 3 is a functional block diagram of an alternative embodiment dental tooth color detector.

FIG. 3 illustrates an alternative embodiment main body assembly 90 for the tooth color detector. This embodiment is essentially the same as the embodiment illustrated in FIG. 2, with the primary exception that the comparison between the detected color signal value on the line 62 and the reference color signal values stored in the color data memory 72 is performed by a processor 92 (i.e., CPU). The numerical designators for the elements from FIG. 2 have been retained in FIG. 3 wherever possible in the interest of clarity and brevity. The processing demands of the present invention will determine the appropriate processor for use in the system. Suitable alternatives may include a processor selected from the 80×86 family of processors, or even an eight bit processor.

The processor 92 is connected to the color data memory 72, program memory 94, scratch pad memory 96 and the display memory 82 via address, data and control buses shown collectively as bus 98. The processor also receives reset and start measurement signals, and the signal on the line 75 indicative of the manufacturer of the restorative material which the dentist is using.

The processor 92 facilitates the use of digital signal processing techniques to determine the restorative material which best matches the color of the tooth. For example, the processor can read a plurality of signal values on the line 62 while the associated LED is illuminated, compute the average or mean of those samples, and compare the average value against the color data stored in the color data memory 72. In addition, the processor allows various built-in-tests to be performed to constantly monitor the operation of the detector.

Figure 4:
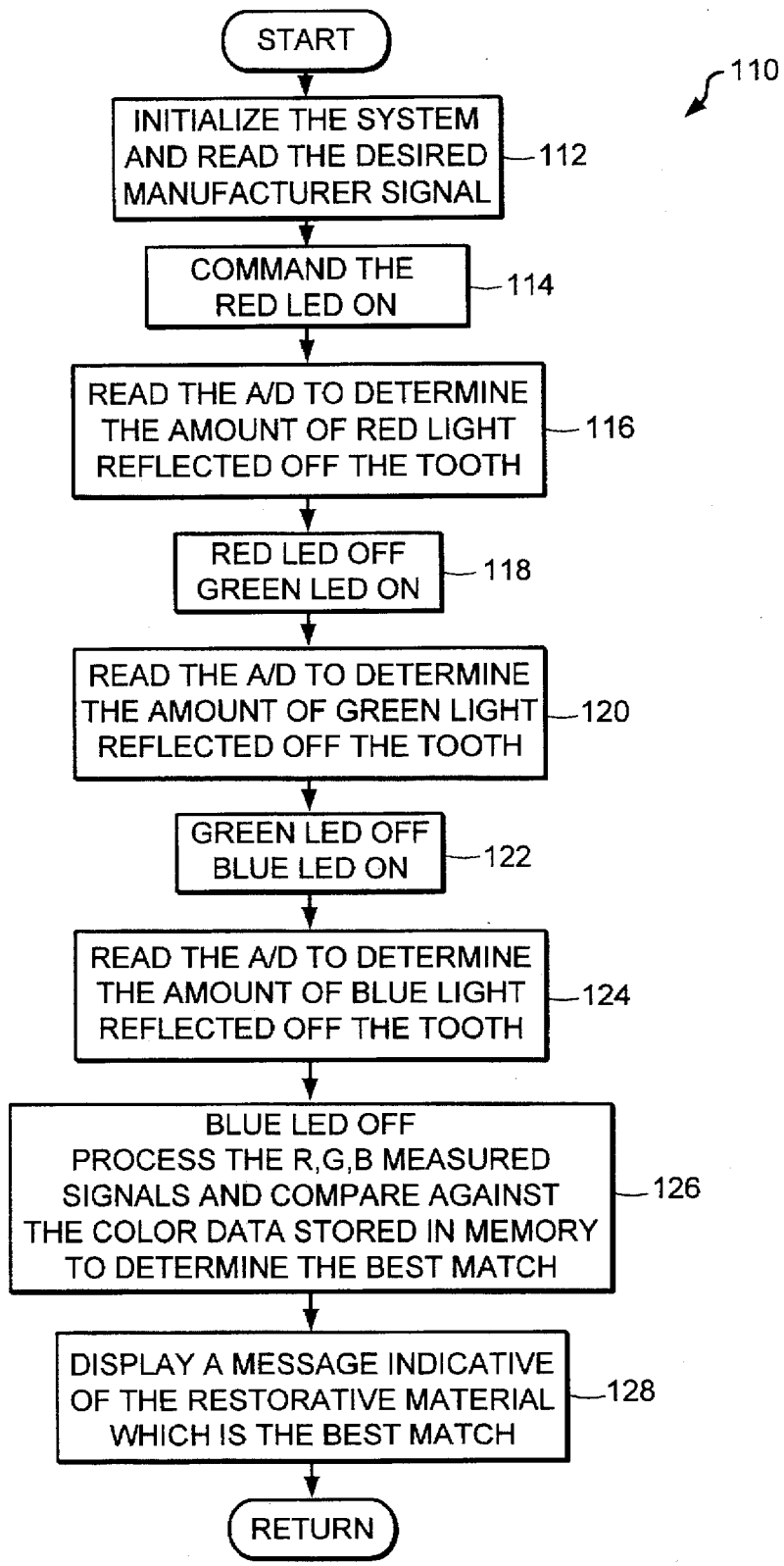
FIG. 4 is flow chart of the processing steps performed by the processor in FIG. 3 to determine the restorative dental material which is the best color match to the tooth.

To control the operation of the detector, the processor 92 executes an application program stored in the program memory 94 (e.g., EPROM or UVPROM). FIG. 4 illustrates a flow chart 110 of a portion of the application program resident in the program memory 94 and executed in the processor 92 when the device is commanded to take a measurement by pushing the start measurement button 32 (FIG. 1). A first step 112 is to initialize the detector and to read the signal on the line 75 (FIG. 3) indicative of the manufacturer. Next step 114 is performed to command the red LED 44 (FIG. 3) on. Step 116 is then performed to read the signal on the line 62 (FIG. 3) indicative of the amount of red light reflected off the tooth. Step 118 is then performed to command the red LED off, and the green LED 45 on. Next, step 120 reads the signal on the line 62 to determine the amount of reflected green light. Steps 122, 124 are then performed to take a similar reading for the blue LED. Once the red, green and blue signals have been read, step 126 is performed to compare the detected color signal against the reference color data stored in the color data memory 72. Step 128 is performed to display an alphanumeric message indicative of the selected restorative material.

An advantage of the embodiment in FIG. 3 is the design flexibility and processing power available with the processor 92. However, processors and memory are relatively expensive, and therefore the embodiment in FIG. 2 may be preferred if its cost is less then the embodiment illustrated in FIG. 3.

Figure 5:
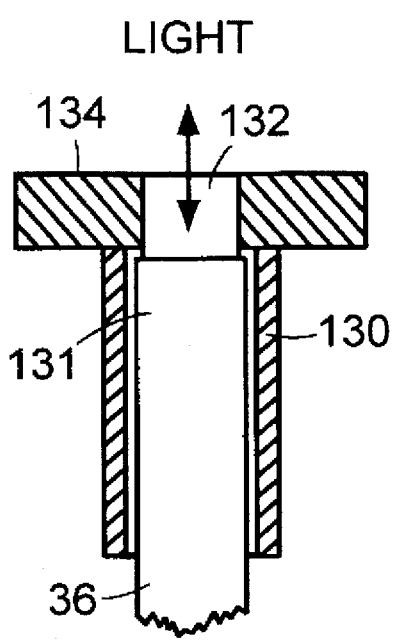
FIG. 5 is a cross sectional view of a protective sheath placed over the wand.

FIG. 5 illustrates a cross sectional view of a protective sheath 130 placed over a tip region 131 of the wand 36 for patient health and safety reasons. The sheath is a disposable and replaceable component which slips over the tip region 131, and includes an opening 132 through which light passes to and from the tip of the wand. Surface 134 is placed against the tooth, and the surface should be formed of a dark light absorbing material which attenuates, and preferably eliminates, the ambient light which enters the opening 132 when placed against the tooth. The surface material should also be relatively compressive thus allowing the surface 134 to deform under force to make completely flush contact against the uneven tooth. In general, the diameter of the surface 134 will be quite small in order to facilitate measuring the color of various sections of the tooth (e.g., the gingival and incisal portions) if necessary. A new sheath should be placed over the wand prior to each new patient.

Although the present invention has been described in the context of a battery powered embodiment, it is contemplated that the device may also be incorporated into the dentist's suite of hard mounted instruments which operate off of standard 120 VAC. In addition, although shown in FIG. 1 as having a fiber optic bundle between the main body assembly 22 and the wand 24, it is further contemplated that the wand and the main body assembly may be incorporated into a single mechanical package thus allowing a user to use the device with one hand.

The digital electronics in the device may also be incorporated into an application specific integrated circuit (ASIC) or a gate array thus increasing the reliability of the system and reducing the power consumption of the detector. In addition, it is contemplated that the LEDs may be replaced with other known light sources such as a single source which provides a broad spectrum of light which can then be filtered to generate the various color components.

It is further contemplated that the detector of the present invention may also include built-in-test logic which monitors the battery power level, and also the integrity of the light being output from the LEDs. Once the battery power drops below a certain level, or the quality of the light from the LEDs is insufficient for proper detector operation, a fault enunciator (e.g., a warning message presented on the display 30) will notify the user of the condition. It is further contemplated that a since each LED is slightly different, a calibration circuit (e.g., with a potentiometer) may also be included to allow the device to be calibrated against a known set of color references. In addition, although the embodiments herein have been discussed in the context of red, green and blue color detection, one of ordinary skill will appreciate that other colors may be used, and that it may be possible to use less than three color components and still achieve the requisite color detection accuracy.

Although the present invention has been shown and described with respect to several preferred embodiments thereof, it should be understood by those skilled in the art that various other changes, omissions, and additions may be made to the embodiments disclosed herein, without departing from the spirit and scope of the present invention.

What is claimed is:

1. A dental tooth color detector which detects the color of a tooth and determines the proper restorative dental material to be used to repair the tooth, said detector comprising:

A. means for illuminating the tooth with light including
      a plurality of light emitting diodes each illuminated in a controlled manner;
      a bifurcated fiber optic bundle having an output path which receives illuminating light from said light emitting diodes, and an input path disposed to provide detected light;
      a light wand which receives the illuminating light from said output path and diffuses the light to provide a diffuse light beam which illuminates the tooth, and which receives reflected light from the tooth and routes said reflected light to said input path;
      a disposable, protective sheath placed over said light wand and comprising a surface which is placed against said tooth, wherein said surface is formed of light absorbing, compressive material;

B. means for detecting a plurality of color components from said detected light which are reflected off the tooth, and for providing a plurality of light color component signal values indicative thereof;

C. means for processing said plurality of color component signal values to determine a desired restorative material which best matches the color of the tooth, wherein said means for processing includes a non-volatile electronic memory device comprising a database of a plurality of reference color signal values indicative of the color characteristics for a plurality of restorative materials, and means for comparing a detected color signal value indicative of said plurality of light color component signal values against said plurality of reference color signal values to determine said desired restorative material; and D. a display for displaying a message indicative of said desired restorative material.

2. The dental tooth color detector of claim 1, wherein said plurality of light emitting diodes includes a red light emitting diode, a green light emitting diode and a blue light emitting diode.

3. The dental tooth color detector of claim 1, wherein only said diodes of a similar color are illuminated at any given moment.

4. A dental tooth color detector which detects the color of a tooth and determines the proper restorative dental material to be used to repair the tooth, said detector comprising:

A. means for illuminating the tooth with light and capturing light reflected from the tooth, including
a light source;
means for receiving illuminating light from said light source and diffusing the light to provide a diffuse light beam which illuminates the tooth, and for receiving reflected light from the tooth;
a disposable, protective sheath placed over a tip portion of said means for receiving and comprising a surface which is placed against said tooth;

B. means for detecting a plurality of color components from said light which are reflected off the tooth, and for providing a plurality of light color component signal values indicative thereof;

C. means for processing said plurality of color component signal values to determine a desired restorative material which best matches the color of the tooth; and D. a display for displaying a message indicative of said desired restorative material.

5. The dental tooth color detector of claim 4, wherein said surface of said disposable, protective sheath is formed of light absorbing, compressive material.

6. The dental tooth color detector of claim 5 wherein said means for processing includes a non-volatile electronic memory device comprising a database of a plurality of reference color signal values indicative of the color characteristics for a plurality of restorative materials, and means for comparing a detected color signal value indicative of said plurality of light color component signal values against said plurality of reference color signal values to determine said desired restorative material.

7. The dental tooth color detector of claim 5 wherein said light source comprises:

a plurality of light emitting diodes each illuminated in a controlled manner, such that only said diodes of a similar color are illuminated at any given moment; and a fiber optic bundle having an output path which receives illuminating light from said light emitting diodes, and an input path disposed to provide light to said means for detecting.

8. The dental tooth color detector of claim 7, wherein said plurality of light emitting diodes includes a red light emitting diode, a green light emitting diode and a blue light emitting diode.

9. The dental tooth color detector of claim 5 said plurality of light color component signal values include signal values indicative of the colors red, green and blue.

10. The dental tooth color detector of claim 5 further comprising:

E. means for receiving a signal value indicative of a selected manufacture's restorative material to be compared against said detected color signal value to determine said desired restorative material.

11. The dental tooth color detector of claim 5 wherein said means for processing comprises a microprocessor.

12. The dental tooth color detector of claim 5 wherein said means for detecting includes a photodetector.

13. The dental tooth color detector of claim 5 wherein said means for processing comprises C4. program memory containing executable software which processes said plurality of light color component signal values to compute a detected color signal value and compares said detected color signal value against said plurality of light color component signal values; and C5. a processor which executes said executable software.

14. The dental tooth color detector of claim 5 wherein said detector is a hand-held battery powered device.

* * * * *